United States Patent [19]

Hargrave et al.

[11] Patent Number: 5,571,806
[45] Date of Patent: Nov. 5, 1996

[54] DIBENZ[B,F][1,4]OXAZEPIN(AND THIAZEPIN)-11(10H)-ONES AND-THIONES AND THEIR USE IN THE PREVENTION OR TREATMENT OF HIV INFECTION

[75] Inventors: Karl D. Hargrave, Brookfield, Conn.; Gunther Schmidt, deceased, late of Munich, Germany, by Margaret Schmidt, legal representative; Wolfhard Engel, Biberach, Germany; Kurt Schromm, Ingelheim am Rhein, Germany

[73] Assignee: Boehringer Ingelheim Pharmaceuticals, Inc., Ridgefield, Conn.

[21] Appl. No.: 271,350

[22] Filed: Jul. 6, 1994

Related U.S. Application Data

[63] Continuation of Ser. No. 53,948, Apr. 28, 1993, abandoned, which is a continuation of Ser. No. 879,652, May 6, 1992, abandoned, which is a continuation of Ser. No. 582,773, Aug. 3, 1990, abandoned, which is a continuation of Ser. No. 400,254, Aug. 29, 1989, abandoned.

[51] Int. Cl.$^6$ .................................................. A61K 31/55
[52] U.S. Cl. ......................................................... 514/211
[58] Field of Search ............................................. 514/211

[56] References Cited

U.S. PATENT DOCUMENTS 4,663,317  5/1987  Albrecht et al. ........................ 514/211

FOREIGN PATENT DOCUMENTS 7002278  4/1980  Japan ............................ A61K 31/55

*Primary Examiner*—Russell Travers
*Attorney, Agent, or Firm*—Robert P. Raymond; Alan R. Stempel; Mary-Ellen M. Devlin

[57] ABSTRACT

Disclosed is the use of dibenz[b,f][1,4]oxazepin (or thiazepin)-11(10H)-ones and -thiones in the prevention and treatment of AIDS, ARC and related disorders associated with HIV infection.

5 Claims, No Drawings

DIBENZ[B,F][1,4]OXAZEPIN(AND THIAZEPIN)-11(10H)-ONES AND -THIONES AND THEIR USE IN THE PREVENTION OR TREATMENT OF HIV INFECTION

This is a continuation, of application Ser. No. 08/053,948 now abandoned, filed Apr. 28, 1993, which is a continuation of application Ser. No. 07/879,652, filed May 6, 1992 (abandoned), which is a continuation of application Ser. No. 07/582,773, filed Aug. 3, 1990 (abandoned), which is a continuation of application Ser. No. 07/400,254, filed Aug. 29, 1989 (abandoned).

FIELD OF THE INVENTION

The invention relates to both known and novel dibenz[b,f][1,4]oxazepin (and thiazepin)-11(10H)-ones and -thiones, and to the use of these compounds in the prevention or treatment of AIDS.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins.

The conversion of the RNA to DNA is accomplished through the use of the enzyme reverse transcriptase (RT), which is included within the infecting virion along with the RNA. Reverse transcriptase has three enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Next, acting as a ribonuclease, RT frees the DNA just produced from the original viral RNA and then destroys the original RNA. Finally, acting as a DNA-dependent DNA polymerase, RT makes a second, complementary, DNA strand, using the first DNA strand as a template. The two strands form double-stranded DNA, the form of DNA found in the host cell's genome, which is integrated into the host cell's genome by another enzyme, called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

SUMMARY OF THE INVENTION

The invention comprises a method for preventing or treating HIV-1 infection which comprises administering, to a human exposed to or infected by HIV-1, a prophylactically or therapeutically effective amount of certain dibenz[b,f][1,4]oxazepin(and thiazepin)-11(10H)-ones and -thiones. A great many of these compounds are known. Some are novel. All possess inhibitory activity against HIV-1RT. The invention further comprises those compounds which are novel and pharmaceutical compositions suitable for the prevention or treatment of HIV-1 infection comprising these novel compounds.

DETAILED DESCRIPTION OF THE INVENTION

A first aspect of the invention comprises a method for preventing or treating HIV-1 infection which comprises administering, to a human who has been exposed to or infected by HIV-1, a prophylactically or therapeutically effective amount of a dibenz[d,f][1,4]oxazepin (or thiazepin)-11(10H)-one or -thione of the formula I

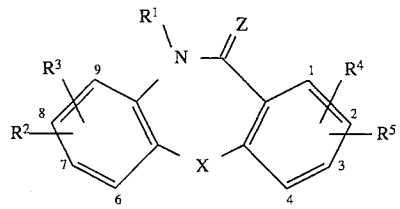

wherein,

X is oxygen or sulfur;

Z is oxygen or sulfur;

$R^1$ is hydrogen, alkyl of 1 to 6 carbon atoms, fluoroalkylmethyl of 1 to 3 fluorine atoms and 2 to 6 carbon atoms, alkenyl or alkynyl of 2 to 6 carbon atoms, mono- or dihalovinyl, cycloalkyl of 3 to 6 carbon atoms, alkyloxyalkyl or alkylthioalkyl of 2 to 6 carbon atoms, alkanoyl of 2 to 4 carbon atoms, arylmethyl or arylmethyloxy or arylcarbonyl (wherein the aryl moiety is phenyl, thienyl or furanyl optionally substituted with methyl, methoxy or halogen), alkoxycarbonylalkyl of 3 to 6 carbon atoms, aminoalkyl of 1 to 3 carbon atoms, mono- or di-alkylaminoalkyl wherein each alkyl moiety contains 1 to 2 carbon atoms, alkanoylamtnoalkyl wherein the alkanoyl moiety contains 2 to 3 carbon atoms and the alkyl moiety contains 1 to 2 carbon atoms, amtnocarbonylalkyl of 2 to 4 carbon atoms, mono- or dfalkylaminocarbonylalkyl wherein each alkyl moiety contains 1 to 2 carbon atoms or hydroxyalkylmethyl of 2 to 6 carbon atoms;

$R^2$ is hydrogen, methyl or halogen;

$R^3$ is hydrogen, alkyl of 1 to 4 carbon atoms, halogen, hydroxyl, alkoxy of 1 to 3 carbon atoms, alkylthio of 1 to 3 carbon atoms, alkanoyloxy of 2 to 3 carbon atoms, amino, alkylamino of 1 to 2 carbon atoms, aminoalkyl of 1 to 2 carbon atoms, mono- or dimethylaminomethyl, hydroxyalkyl of 1 to 4 carbon atoms, alkoxyalkyl wherein each alkyl moiety contains 1 to 2 carbon atoms, alkylthioalkyl wherein each alkyl moiety contains 1 to 2 carbon atoms, carboxylalkyl of 2 to 4 carbon atoms, carboxyalkoxy of 2 to 3 carbon atoms, alkoxycarbonylmethyl of 3 to 4 carbon atoms or methoxycarbonylmethoxy;

$R^4$ is hydrogen, methyl or halogen; and, $R^5$ is hydrogen, alkyl of 1 to 4 carbon atoms, halogen, hydroxyl, alkoxy of 1 to 3 carbon atoms, alkylthio of 1 to 3 carbon atoms, alkanoyloxy of 2 to 3 carbon atoms, amino or alkylamino of 1 to 2 carbon atoms (excepting 4-amino and 4-alkylamino), aminoalkyl of 1 to 2 carbon atoms, mono- or dimethylaminomethyl, hydroxyalkyl of 1 to 4 carbon atoms, alkoxyalkyl wherein each alkyl moiety contains 1 to 2 carbon atoms, carboxylalkyl of 2 to 4 carbon atoms, carboxyalkoxy of 2 to 3 carbon atoms, alkoxycarbonylmethyl of 3 to 4 carbon atoms or methoxycarbonylmethoxy;

or a pharmaceutically acceptable salt thereof.

In a subgeneric aspect, the invention comprises the above-described method wherein, in the compound of formula I, X is oxygen or sulfur;

Z is oxygen;

$R^1$ is alkyl of 1 to 5 carbon atoms, fluoroalkylmethyl of 1 to 3 fluorine atoms and 2 to 5 carbon atoms, alkenyl or alkynyl of 2 to 5 carbon atoms, mono- or dihalovinyl, cycloalkyl of 3 to 6 carbon atoms, alkyloxymethyl or alkylthiomethyl of 2 to 5 carbon atoms, alkoxyethyl or alkylthioethyl of 3 to 5 carbon atoms, alkanoyl of 2 to 3 carbon atoms, arylmethyl (wherein the aryl moiety is phenyl, thienyl or furanyl, optionally substituted with methyl, methoxy or halogen), alkoxycarbonylmethyl of 3 to 5 carbon atoms, acetylaminoalkyl wherein the alkyl moiety contains 1 to 2 carbon atoms, alkoxy of 1 to 4 carbon atom or hydroxyalkylmethyl of 2 to 5 carbon atoms;

$R^2$ is hydrogen, methyl or halogen;

$R^3$ is hydrogen, alkyl of 1 to 3 carbon atoms, halogen, hydroxyl, methoxy, ethoxy, methylthio, ethylthio, alkanoyloxy of 2 to 3 carbon atoms, amino, methylamino, aminoalkyl of 1 to 2 carbon atoms, mono- or dimethylaminomethyl, hydroxyalkyl of 1 to 3 carbon atoms, alkoxyalkyl wherein each alkyl moiety contains 1 to 2 carbon atoms, alkylthioalkyl wherein each alkyl moiety contains 1 to 2 carbon atoms, carboxyalkyl of 2 to 3 carbon atoms, carboxyalkoxy of 2 to 3 carbon atoms, alkoxycarbonylmethyl of 3 to 4 carbon atoms or methoxycarbonylmethoxy;

$R^4$ is hydrogen, methyl or halogen; and, $R^5$ is hydrogen, alkyl of 1 to 3 carbon atoms, halogen, hydroxyl, methoxy, ethoxy, methylthio, ethylthio, alkanoyloxy of 2 to 3 carbon atoms, amino or methylamino (excepting 4-amino and 4-methylamino), aminoalkyl of 1 to 2 carbon atoms, alkoxyalkyl or alkylthioalkyl wherein each alkyl moiety contains 1 to 2 carbon atoms, carboxyalkoxy of 2 to 3 carbon atoms, carboxyalkoxy of 2 to 3 carbon atoms, alkoxycarbonylmethyl of 3 to 4 carbon atom or methoxycarbonylmethoxy.

In a further subgeneric aspect, the invention comprises the above described method wherein, in the compound of formula I, X is oxygen or sulfur;

Z is oxygen;

$R^1$ is alkyl of 1 to 4 carbon atoms, fluoroalkylmethyl of 1 to 3 fluorine atoms and 2 to 4 carbon atoms, alkenylmethyl or alkynylmethyl of 2 to 4 carbon atoms, mono- or 1,2-dihalovinyl, alkoxymethyl or alkylthiomethyl of 2 to 4 carbon atoms, alkoxyethyl or alkylthioethyl of 3 to 4 carbon atoms or alkoxycarbonylmethyl of 3 to 4 carbon atoms;

$R^2$ is hydrogen, methyl or chlorine;

$R^3$ hydrogen, methyl, ethyl, chlorine, bromine, hydroxyl, methoxy, methylthio, acetyloxy, amino, methylamino, aminomethyl, hydroxymethyl, hydroxyethyl, methoxymethyl or methylthiomethyl;

$R^4$ is hydrogen, methyl or chlorine; and, $R^5$ is hydrogen, methyl, ethyl, chlorine, bromine, hydroxyl, methoxy, methylthio, acetyloxy, amino or methylamino (excepting 4-amino and 4-methylamino), aminomethyl, hydroxymethyl, hydroxyethyl, methoxymethyl or methylthiomethyl.

In a still further subgeneric aspect, the invention comprises the above described method wherein, in the compound of formula I, X is oxygen or sulfur;

Z is oxygen;

$R^1$ is alkyl of 1 to 4 carbon atoms, fluoroalkylmethyl of 1 to 3 fluorine atoms and 2 to 4 carbon atoms, alkenylmethyl or alkynylmethyl of 2 to 4 carbon atoms, mono- or 1,2-dihalovinyl, alkoxymethyl or alkylthiomethyl of 2 to 4 carbon atoms, alkoxyethyl or alkylthioethyl of 3 to 4 carbon atoms or alkoxycarbonylmethyl of 3 to 4 carbon atoms;

$R^2$ and $R^4$ are each hydrogen;

$R^3$ is hydrogen or 7-methyl; and, $R^5$ is hydrogen or 2-amino.

Compounds of formula I are either known or can be prepared using methods analogous to those used to prepare known compounds. Representative compounds of formula I and methods for their preparation are described, for example, in the following prior art references: U.S. Pat. Nos. 3,367,930; 3,541,085; 3,546,214; and, 4,379,150; and British Patent Nos. 1,164,579 and 1,170,322.

Compounds of formula I, can additionally be prepared according to the following general methods A, B and C.

Method A

Compounds of Formula I, wherein Z is oxygen and X and $R^1$–$R^5$ have the meanings given above with the exception of $R^1$ being hydrogen, may be obtained, for example, by converting a compound of the formula II

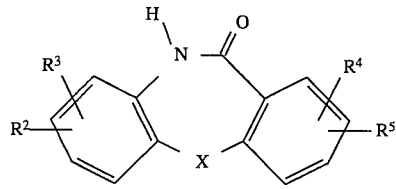

wherein $R^2$–$R^5$ are as defined above, into the corresponding alkali or alkaline earth methal compounds of the formula III

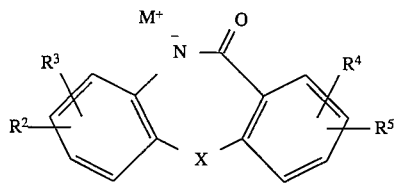

wherein $R^2$–$R^5$ are as defined above, and subsequently reacting, without isolation, this alkali metal compound with a reactive alkylating or acylating reagent of the formula IV $R^1$ Y  IV wherein $R^1$ has the meanings given above except for hydrogen and Y is a suitable leaving group such as chloride, bromide, iodide, an alkyl or arylsulfonate, or an alkyl- or arylcarbonyloxy group under well known alkylating or acylating conditions.

It will be obvious to those skilled in the art that the presence of nucleophilic substituents in compounds of formula II, for example, will require the use of an intermediate having substituents which are, other than the 5-position nitrogen, not nucleophilic but which can be derivatized to yield the required group. For example, amino or monoalkylamino substituents are preferably obtained by alkylating or acylating an intermediate of formula II having nitro group(s) at the desired positions, and subsequently reducing the nitro group(s), and alkylating, if appropriate, to yield the final product.

Method B

Compounds of formula I wherein Z is oxygen and X and $R^1$–$R^5$ are as defined above may be obtained by cyclization of compounds of the formula V

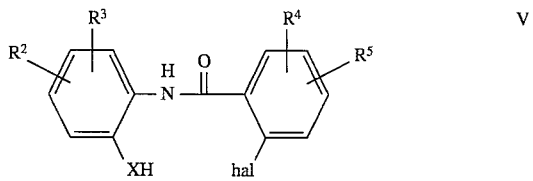

wherein X and $R^2$–$R^5$ are as defined above and hal is fluorine, chlorine, bromine or iodine, preferably in the presence of an inorganic base, such as sodium or potassium hydride, lithium alkyls such as n-butyl lithium, sodium or potassium hydroxide, or in the presence of an organic base such as quinoline or 4-(N,N-dimethylamino)pyridine, at ambient or elevated temperatures, preferably 80°–175° C., up to the boiling point of the reaction mixture. In those cases where $R^1$ is hydrogen, 2 equivalents of base should be used. Suitable solvents include inert aprotic solvents such as sulfolane or dimethylformamide.

The diphenylamides of formula V may be obtained, for example, by condensing suitably substituted ortho halobenzoic acid chlorides of the formula VI

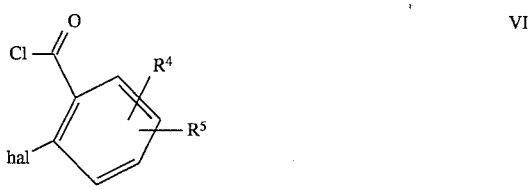

wherein hal may be fluorine, chlorine, bromine or iodine and $R^4$ and $R^5$ are as defined above, with ortho-amino-phenols (or thiophenols) of the formula VII

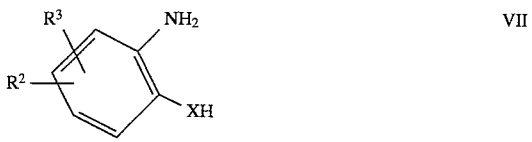

wherein X, $R^2$ and $R^3$ are as defined above, under well-known reaction conditions. Depending upon the reaction conditions employed and the nature of X and $R^2$–$R^5$, tricyclic compounds of the formula II, may be formed in one step, without the isolation of the amide of formula V, by the condensation of compounds of the formulas VI and VII. This single-step formation of the tricyclic compounds is most readily effected when X is sulfur and at elevated temperatures, especially in the range of 125°–200° C.

Method C

Thiolactams of the general formula I, wherein X and $R^1$–$R^5$ are as defined above, can be obtained by treatment of lactams of the formula I with sulfurating reagents such as 2,4-bis(4-methoxyphenyl)-1,3-dithia-2-4-diphosphetane-2, 4-disulfide, bis(tricyclohexyltin)sulfide, bis(tri-n-butyltin)sulfide, bis(triphenyltin)sulfide, bis(trimethylsilyl)sulfide and phosphorous pentasulfide. The reaction is generally carried out under anhydrous conditions in inert organic solvents such as carbon disulfide, benzene or toluene, at room temperature or, preferably, at higher temperatures up to the boiling point of the reaction mixture. When using the above mentioned tin or silyl sulfides it is preferable to carry out the sulfurization reaction in the presence of a Lewis acid such as boron trichloride.

It will be obvious to those skilled in the art that the presence of another carbonyl moiety in a compound of formula I, for example, a compound wherein Z is oxygen and any of $R^2$ to $R^5$ is alkanoyl, will require that the ketone carbonyl be protected via known methods by a suitable protecting group (such as ethylene glycol) prior to the sulfurization reaction; deprotection subsequent to the sulfurization reaction provides the desired compound. Similarly, in cases wherein $R^1$ is, for example, acetyl, it will be obvious that the sulfurization reaction should be performed prior to the acylation (of N-5). In those cases wherein the substituents at $R^2$ to $R^5$ can be derived from nitro, for example, alkanoylamino, the sulfurization reaction can be performed on the corresponding nitro derivative, followed by an appropriate (known) reduction and finally acylation to yield the desired product.

Compounds of formula I having basic or acidic substituents may, if desired, be converted into their pharmaceutically acceptable salts by conventional methods.

Examples of inorganic and organic acids which may form pharmaceutically acceptable acid addition salts with a compound of formula I having basic substituents are the following: hydrochloric acid, hydrobromic acid, sulfuric acid, phosphoric acid, nitric acid, tartaric acid, citric acid, methanesulfonic acid and the like.

Examples of bases which may form pharmaceutically acceptable salts with compounds of formula I having acidic substituents are the following: sodium hydroxide, potassium hydroxide, calcium hydroxide, ammonia, tromethamine and the like. The above described compounds of formula I inhibit HIV-1 reverse transcriptase and thereby inhibit HIV-1 replication, making them useful in the method which constitutes one aspect of the invention.

In carrying out this method, the compounds of formula I may be administered in single or divided doses by the oral, parenteral or topical routes. A suitable oral dosage for such compounds would be in the range of about 10 to 500 mg per day. In parenteral formulations, a suitable dosage unit may contain from 1 to 50 mg of said compounds, whereas for topical administration, formulations containing 0.01 to 1% active ingredient are preferred. It should be understood, however, that the dosage administration will vary from patient to patient and the dosage for any particular patient will depend upon the clinician's judgement, who will use as criteria for fixing a proper dosage the size and condition of the patient as well as the patient's response to the drug.

When such compounds are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkyleneglycols, petroleum jelly and the like. The pharmaceutical preparations can be prepared in a conventional manner and finished dosage forms can be solid dosage forms, for example, tablets, dragees, capsules, and the like, or liquid dosage forms, for example, solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers, such as polyethylene glycol.

For parenteral use, it is preferred to administer such compounds in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds can also be administered as solutions for nasal applications which may contain, in addition to the compounds, suitable buffers, tonicity adjusters, microbial preservatives, antioxidants and viscosity- increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chlorobutanol or phenylethyl alcohol.

Additionally, such compounds can be administered by suppository.

As stated before, the compounds of formula I inhibit the enzymatic activity of HIV-1 RT. Based upon testing of these compounds, as described below, it is known that they inhibit the RNA-dependent DNA polymerase activity of HIV RT. It is believed that they also inhibit the DNA-dependent DNA polymerase activity of HIV RT.

Utilizing the Reverse Transcriptase (RT) Assay described below, compounds can be tested for their ability to inhibit the RNA-dependent DNA polymerase activity of HIV RT. Certain specific compounds, described in the Examples which appear below, were so tested. The results of this testing appear in Table I, below.

REVERSE TRANSCRIPTASE (RT) ASSAY

Assay Theory

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate.

Materials a) Preparation of the enzyme

Reverse transcriptase enzyme from the LAV strain of Human Immuno-deficiency Virus (HIV-1) (1) was isolated from the bacterial strain JM109 (3) expressing the DNA clone pBRTprtl+(2) which is under the control of the lac promotor in the expression vector pIBI21 (4). An overnight culture grown in 2XYT medium (37° C., 225 rpm) (5) supplemented with 100 mg/ml ampicillin for positive selection is inoculated at a 1:40 dilution into M9 medium supplemented with 10 mg/ml thiamine, 0.5% casamino acids, and 50 mg/ml ampicillin (5). The culture is incubated (37° C., 225 rpm) until it reaches an OD540 of 0.3–0.4. At that time the repressor inhibitor IPTG (isopropyl b-D-thiogalactopyranoside) is added to 0.5 mM and incubated for 2 additional hours. Bacteria are pelleted, resuspended in a 50 mM Tris, 0.6 mM EDTA, 0.375M NaCl buffer and digested by the addition of lysozyme (1 mg/ml) for 30 minutes on ice. The cells are lysed by the addition to 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mMDTT, 0.1% NP-40, 0.1M NaCl, and 50% glycerol) and stored at −70° C. for further use.

b) Composition of 2X concentrated stock reaction mixture

| Stock Reagent | 2X Mix Concentration |
| --- | --- |
| 1M Tris pH 7.4 | 100 mM |
| 1M Dithiothrietol | 40 mM |
| 1M NaCl | 120 mM |
| 1% Nonidet P-40 | 0.1% |
| 1M MgCl | 4 mM |
| [poly r(C)/oligo d(G)](5:1) | 2 mg/ml |
| $^3$H-dGTP (81 µM) | 0.6 mM |

Assay Procedure

The 2X concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 µl/well; 3 wells/compound). The HIV RT enzyme is thawed, diluted in 50 mM Tris pH 7.4 so that fifteen µl of diluted enzyme contain 0.001 Unit (one unit is that amount of enzyme to transform 1 micromole of substrate per minute at 25° C.), and 15 µl are dispensed per well. Twenty µl of 0.12–0.5M EDTA are added to the first three wells of the microtiter plate. EDTA chelates the Mg$^{++}$ present and prevents reverse transcription. This group serves as background polymerization which is subtracted from all other groups. Twenty-five µl of the 2X reaction mixture are added to all wells and the assay is allowed to incubate at room temperature for 60 minutes. The assay is terminated by precipitating the DNA in each well with 50µl of 10% trichloracetic acid (TCA) in 1% sodium pyrophosphate. The microtiter plate is incubated for 15 minutes at 4° C. and the precipitate is fixed onto #30 glass fiber paper (Schleicher & Schuell) using a Skatron semi-automatic harvester. The filters are then washed with additional 5% TCA containing 1% sodium pyrophosphate, rinsed with 70% aqueous ethanol, dried, and transferred to scintillation vials (6). Each vial receives 2 mls of scintillation cocktail and is counted in a Beckman beta counter.

Calculations for percent inhibition are as follows:

% inhibition =

$$\frac{CPM \text{ Mean Test Value} - CPM \text{ Mean Control Value} \times 100}{CPM \text{ Mean Control Value}}$$

References

1. Benn, S., et al., SCIENCE 230:949, 1985
2. Farmerie, W. G. et. al., SCIENCE 236:305, 1987
3. Yanisch-Perron, C., Viera, J., and Messing, J., 3., GENE 33:103, 1985
4. International Biotechnologies, Inc., New Haven, Conn. 06535
5. Maniatis, T, Fritsch, E. F., and J. Sambrook, eds. MOLECULAR CLONING: A LABORATORY MANUAL, Cold Spring Harbor Laboratory, 1982
6. Spira, T., et. al. J. Clinical Microbiology, 25:97, 1987.

In order to confirm that compounds which are active in the RT Assay also have the ability to inhibit HIV replication in a living system, a compound of formula I was also tested in the human T-Cell Culture Assay described below. The results of this test appears in Table II.

HUMAN T CELL CULTURE ASSAY

Assay Theory: Formation of syncytia is a feature of in vitro cultures of CD4+ T-cells infected with HIV-1. In this assay, T-cells are treated with a putative replication inhibiting compound and then infected with HIV-1. After incubation the culture is checked for the formation of syncytia. The absence or reduction is the number of syncytia is used as a measure of the test compound's ability to inhibit HIV replication.

Assay Method: The target cells, designated C8166, are a subclone of human lymphoma cells of T-cell origin and are established at an initial density of $5 \times 10^4$ per 100 µl in RPMI 1640 (+10% fetal bovine serum) culture medium in 96 well flat bottom plates. A selected amount of test compound, dissolved in DMSO is included. After 24 hours, 50–100 $TCID_{50}$'s (the dose that results in induced effect in 50% of test cultures) of the HTLV-IIIB strain of HIV-1 (2) are innoculated into each culture. Control cultures receive compound or virus only. Four days after virus challenge, cultures are visually examined for the frequency and distribution of virus-induced giant cell syncytia. The percent inhibition by the test compound is determined by comparison with control values. Confirmation of the presence or absence of virus replication is accomplished by harvesting the cell free culture fluids from all experimental groups to determine the presence or absence of infectious progeny through the induction of syncytia formation in secondary human T-cell cultures after 3 days.

References (1) M. Somasundaran and H. L. Robinson, Science 242, 1554 (1998)

(2) G. M. Shaw, R. H. Hahn, S. K. Arya, J. E. Groopman, R. C. Gallo and F. Wong-Staal, Science 226, 1165 (1984)

In order to assess the specificity of the enzyme inhibitory activity of the compounds of formula I, a few were tested, using known per se assay methods, for their ability to inhibit Feline Leukemia Virus-derived reverse transcriptase and Calf Thymus-derived DNA alpha-polymerase. None of the compounds so tested was observed to possess any inhibitory activity against these enzymes. These results indicate that the enzyme inhibitory activity of the compounds provided by the invention is directed rather specifically against HIV RT.

In order to roughly assess the cytotoxicity of the compounds of formula I, two such compounds were tested in the MTT Cellular Cytotoxicity Assay described below. The results of this testing are reported in Table II, below. Compounds having a relatively high $EC_{50}$ are preferred.

MTT ASSAY FOR CELLULAR CYTOTOXICITY

Assay Theory

The MTT (3-(4,5-dimethylthiazol-2yl)-2,5 diphenyl tetrazolium bromide) assay is based on cleavage of tetrazolium bromide by metabolically active cells, resulting in a highly quantitative blue color. This assay has been previously described (1) but has been optimized for the purposes of the testing reported herein.

Assay Method

The H9 cell line (2), an established human lymphoma suspension cell line grown in RPMI 1640 supplemented with 10% fetal bovine serum is used as the target cell line in the assay. Cells (100 µl) are plated in microtest plate wells at a concentration of $10^5$ cells per ml in the presence of varying concentrations of inhibitor. The cells are incubated at 37° C. in a humidified $CO_2$ incubator. Five days later, 20 µl of MTT (5 mg/ml in RPMI 1640, sonicated, 0.2 micron filtered, and stored at 4° C.) is added to each well. After 4 hours additional incubation at 37° C., 60 µl of Triton-X is added to each well and thoroughly mixed to aid the solubilization of the crystals. Absolute ethanol (5 µl) is added to each well to remove bubbles and the resulting mixture is incubated for 30 minutes at 60° C. and immediately read on a plate reader (Dynatech) at a wavelength of 570 nm.

Data from this assay are used to generate a nonlinear regression analysis which yields an $EC_{50}$.

References

1. Mosmann, Tim, J. Immunol. Methods, 65:55, 1983.
2. Jacobs, J. P., J. Natl. Cancer Inst., 34:231, 1965.

TABLE I

| Compound of Example | $R^1$ | Other Substituents* | RT Inhibition (% @ 10 µg/ml) |
|---|---|---|---|
| 1 | $CH_2CH_2CH_3$ | | 100 |
| 2 | $CH(CH_3)_2$ | | 100 |
| 3 | $CH_2CH_2CH_3$ | Z=S | 94 |
| 4 | H | X=S | 43 |
| 5 | $CH_2CH_2CH_3$ | X=S | 98 |
| 6 | $CH_3$ | 2-$NH_2$, 7-$CH_3$ | 100 |
| 7 | H | | 22 |
| 8 | $CH_2CH_3$ | | 100 |
| 9 | $CH_2CH=CH_2$ | | 98 |
| 10 | $CH_3$ | | 93 |
| 11 | $CH_2C(CH_3)=CH_2$ | | 77 |
| 12 | $COCH_2CH_3$ | | 44 |
| 13 | $CH_2CONH_2$ | 4-$OCH_3$ | 32 |

TABLE I-continued

| Compound of Example | R¹ | Other Substituents* | RT Inhibition (% @ 10 μg/ml) |
|---|---|---|---|
| 14 | H | 2-NH$_2$ | 85 |
| 15 | CH$_2$CONH$_2$ | 2-NH$_2$ | 82 |
| 16 | CH$_2$CH$_3$ | 2-NH$_2$ | 100 |
| 17 | H | 2-NH$_2$, 8-Cl | 67 |
| 18 | H | 2-NH$_2$, 8-CH$_3$ | 71 |
| 19 | CH$_2$CH$_3$ | 2-NH$_2$, 8-CH$_3$ | 100 |
| 20 | CH$_2$CH$_3$ | 2-NH$_2$, 8-Cl | 95 |
| 21 | H | 7-NH$_2$ | 3 |
| 22 | CH$_3$ | 2-NH$_2$ | 99 |
| 23 | H | 3-NH$_2$ | 25 |
| 24 | CH$_3$ | 7-NH$_2$ | 44 |
| 25 | CH$_3$ | 3-NH$_2$ | 26 |
| 26 | CH$_3$ | 2-NHCH$_3$ | 75 |
| 27 | CH$_2$CH=CH$_2$ | 2-NH$_2$ | 100 |
| 28 | H | 2-NHCH$_3$ | 30 |
| 29 | CH$_2$CH=CH$_2$ | 7-NH$_2$ | 89 |
| 30 | H | 2-NH$_2$, 7-CH$_3$ | 96 |
| 31 | CH$_2$CONH$_2$ | 7-CH$_3$ | 77 |
| 32 | CH$_3$ | 7-OCH$_2$CH$_3$ | 77 |
| 33 | CH$_2$CH$_3$ | 7-OCH$_2$CH$_3$ | 74 |
| 34 | CH$_2$SCH$_3$ | | 100 |
| 35 | CH$_2$SOCH$_3$ | | 58 |
| 36 | CH$_2$CH$_2$SCH$_3$ | | 85 |
| 37 | CH$_2$SCH$_3$ | 3-Cl | 98 |
| 38 | CH$_2$CH$_2$SCH$_3$ | 3-Cl | 83 |
| 39 | CH$_2$CH$_2$SCH$_3$ | 7-CH$_3$ | 95 |
| 40 | CH$_2$SOCH$_3$ | 7-CH$_3$ | 77 |
| 41 | CH$_2$CH$_2$SCH$_3$ | 2-Cl | 49 |
| 42 | H | 7-OCH$_2$CH$_3$ | 30 |
| 43 | CH$_2$CO$_2$CH$_2$CH$_3$ | | 76 |
| 44 | H | 7-OCH$_3$ | 27 |
| 45 | H | 1,7-(OCH$_3$)$_2$ | 44 |
| 46 | CH$_2$CH$_2$F | | 93 |
| 47 | CF=CHI | | 92 |
| 48 | CH$_2$CF$_3$ | | 87 |
| 49 | CH$_3$ | X=S | 94 |
| 50 | CH$_2$CONH$_2$ | X=S | 66 |

*X and Z are each oxygen unless otherwise noted.

*X and Z are each oxygen unless otherwise noted.

TABLE II

| Compound of Example | T-Cell Culture Assay (% inhibition) | Cytotoxity Assay (EC$_{50}$) |
|---|---|---|
| 1 | 93 | 20 |
| 5 | NT | 10 |

Note:
NT = not tested

The following examples further illustrate the present invention and will enable others skilled in the art to understand the invention more completely. It should be understood, however, that the invention is not limited to the particulars given in the examples.

EXAMPLE 1

10-Propyl-10H-Dibenz[b,f][1,4]Oxazepin-11-One

To a solution of 3.0 grams of 10H-dibenz[b,f][1,4]oxazepin-11-one in 50 ml of dry dimethylformamide was added 0.82 grams of a 50% dispersion of sodium hydride in mineral oil. The resulting mixture was stirred for one hour and 3.7 grams of 1-bromopropane was then added slowly. The reaction mixture was stirred for 3 hours and the excess sodium hydride decomposed by the addition of ice. After further dilution with water the product was extracted with ether, dried (anhydrous sodium sulfate) and concentrated. The resulting oil was purified on a silica gel column (ethyl acetate/hexane, 1:4) to provide 3.1 grams (87% of theory) of 10-propyl-10H-dibenz[b,f][1,4]oxazepin-11-one as a colorless oil.

EXAMPLE 2

10-Isopropyl-10H-Dibenz[b,f][1,4]Oxazepin-11-One

Following the proceedure described in Example 1, 3.0 grams of 10H-dibenz[b,f][1,4]oxazepin-11-one and 3.7 grams of 2-propyl bromide were reacted in the presence of 0.82 grams of a 50% dispersion of sodium hydride in mineral oil and 50 ml of dry dimethylformamide. The product was purified on the silica gel column (ethyl acetate/hexane, 1:4). The resulting oil was dissolved in petroleum ether which on standing gave 1.33 grams (30% of theory) of 10-isopropyl-10H-dibenz[b,f][1,4]oxazepin-11-one as colorless needles, m.p. 102°–103° C.

EXAMPLE 3

10-Propyl-10H-Dibenz[b,f][1,4]Oxazepin-11-Thione

A mixture of 2.45 grams of 10-propyl-10H-dibenz[b,f][1,4]oxazepin-11-one, prepared as in Example 1, 2.02 grams of Lawesson(s) reagent and 50 ml of toluene was refluxed for 5 hours. The solvent was then removed in vacuo to give a yellow oil which was purified on a silica gel column (ethyl acetate/hexane, 1:5) to give 1.05 grams (57% of theory) of 10-propyl-10H-dibenz[b,f][1,4]oxazepin-11-thione as a yellow oil.

EXAMPLE 4

Dibenz[b,f][1,4]Thiazepin-11(10H)-One

A mixture of 1.4 grams of 2-aminothiophenol, 2.5 grams of 2-iodobenzoic acid, 0.5 grams of copper bronze, 2.6 grams of potassium hydroxide and 15 ml of water were refluxed under nitrogen for 5½ hours. The mixture was then filtered and the filtrate acidified with concentrated hydrochloric acid, stirred for 1 hour and the solid collected by suction filtration. After washing with ethanol and diethyl ether, the solid was dried in vacuo to give 2.1 grams (75% of theory) of 2-[(2'-aminophenyl)thiol]benzoic acid as an off white powder, m.p. 220° C. (dec.) suitable for use in the next reaction. The amino acid described above was heated neat to 200°–230° C. for 4 hours. Crystallization from ethyl acetate provided 0.22 grams (23% of theory) of dibenz[b,f][1,4]thiazepin-11(10H)-one as a light beige crystalline power, m.p. 258°–259° C.

EXAMPLE 5

10-n-Propyl-Dibenz[b,f][1.4]Thiazepin-11(10H)-One 0.14 grams of a 50% dispersion of sodium hydride in mineral oil was added to a solution of dibenz[b,f][1,4]thiazepin-11(10H)-one in 10 ml of dimethylformamide. After 15 minutes the mixture was warmed to 50° C. and stirred under argon for one hour. After allowing the mixture to cool to room temperature, 0.34 grams of 1-bromopropane was added slowly. The reaction mixture was stirred for 5 hours, after which time it was quenched with water and the product extracted with diethyl ether. The extracts were washed with a saline solution, dried (anhydrous magnesium sulfate) and concentrated to give a colorless oil which was purified by column chromatography (ethyl acetate/hexane, 5%, 10%, 20%) to provide 0.37 grams (91% of theory) of 10-n-propyl-dibenz[b,f][1,4]thiazepin-11(10H)-one as a white crystalline solid, m.p. 103°–104.5° C.

EXAMPLE 6

2-Amino-7,10-Dimethyldibenz[b,f][1,4]Oxazepin-11(10H)-One a) 2-Nitro-7-methyl-dibenzo[b,f][1,4]oxazepin-11(10H)-One A mixture of 20.2 g (0.1 mole) of 2-chloro-5-nitrobenzoic acid and 8.4 ml thionyl chloride in 100 ml of dioxane was refluxed for 90 minutes. The solution was cooled to 50° C. and added to a suspension of 12.3 g (0.1 mole) of 2-amino-5-methyl phenol in 50 ml of water. After about half of the acid chloride was added, 8.2 g sodium acetate was added, then the rest of the acid chloride was added dropwise. The reaction mixture was stirred for 45 minutes at 50° C. Ice water was added to the mixture with stirring, and the resulting precipitate was filtered and washed with water. The filter cake was dissolved in 150 ml of water containing 4 g of NaOH and stirred for 1 hour at 85°–95° C., then cooled to room temperature. The cooled solution was acidified with HCl, filtered, and washed with water. The precipitate was dried to yield 11.3 g (42%) of 2-nitro-7-methyldibenz[b,f][1,4]oxazepin-11(10H)-one, mp 264°–266° C.

b) 2-Nitro-7,10-dimethyldibenz[b,f][1,4oxazepin-11(10H)-one

To a warm solution of 4.05 g potassium methoxide in 80 ml of t-butanol and 80 ml of dioxane was added 13.5 g (0.05 mol) of 2-nitro-7-methyldibenz[b,f][1,4]oxazepin-11(10H)-one. The resulting suspension was warmed to 60° C. for 15 minutes. Initially everthing went in solution, after several minutes a crystalline precipitate formed. To the stirred suspension was added 3.75 ml of iodomethane. The reaction mixture was stirred for 4 hours at 60° C., then concentrated to dryness in vacuo. The dark residue was suspended in water, acidified with acetic acid, concentrated in vacuo and then recrystallized from propanol to give 8.5 g (60% yield) of 2-nitro-7,10-dimethyldibenz[b,f][1,4]-oxazepin-11(10H)-one mp 156°–159°.

c) 2-Amino-7,10-dimethyldibenz[b,f][1,4]benzoxazepin-11(10H)-one

A mixture of 8.5 g (0.03 mole) of 2-nitro-7,10-dimethylbenzoxazepin-11(10H)one in 100 ml of ethanol and 3 g Raney Nickel was hydrogenated at 50° C. and 50 atm. The hydrogenation mixture was heated to boiling and filtered. The filtrate was cooled and the crystalline precipitant filtered off to give 4.4 g (58%) of 2-nitro-7,10-dimethyldibenz [b,f][1,4]oxazepin- 11(10H) -one, mp 183°–185° C.

EXAMPLES 7–50

Using synthetic methods analogous to those described above, the following compounds were prepared:

| Compound of Example | $R^1$ | Other Substituents* | Melting Points (°C.) |
|---|---|---|---|
| 7 | H | | 211–213 |
| 8 | $CH_2CH_3$ | | 53–54 |
| 9 | $CH_2CH=CH_2$ | | 89–91 |
| 10 | $CH_3$ | | 81–82 |
| 11 | $CH_2C(CH_3)=CH_2$ | | 83–84 |
| 12 | $COCH_2CH_3$ | | 78–80 |
| 13 | $CH_2CONH_2$ | 4-$OCH_3$ | 238–240 |
| 14 | H | 2-$NH_2$ | 200–202 |
| 15 | $CH_2CONH_2$ | 2-$NH_2$ | 224–225 |
| 16 | $CH_2CH_3$ | 2-$NH_2$ | 165–166 |
| 17 | H | 2-$NH_2$, 8-Cl | 266–267 |
| 18 | H | 2-$NH_2$, 8-$CH_3$ | 169–170 |
| 19 | $CH_2CH_3$ | 2-$NH_2$, 8-$CH_3$ | 114–115 |
| 20 | $CH_2CH_3$ | 2-$NH_2$, 8-Cl (HCl salt) | 255 (dec) |
| 21 | H | 7-$NH_2$ | NA |
| 22 | $CH_3$ | 2-$NH_2$ | 133–136 |
| 23 | H | 3-$NH_2$ | 287–289 |
| 24 | $CH_3$ | 7-$NH_2$ | 184–186 |
| 25 | $CH_3$ | 3-$NH_2$ | 187–189 |
| 26 | $CH_3$ | 2-$NHCH_3$ | 132–134 |
| 27 | $CH_2CH=CH_2$ | 2-$NH_2$ | 156–158 |
| 28 | H | 2-$NHCH_3$ | 175–177 |
| 29 | $CH_2CH=CH_3$ | 7-$NH_2$ | 112.5–115.5 |
| 30 | H | 2-$NH_2$, 7-$CH_3$ | 184–186.5 |
| 31 | $CH_2CONH_2$ | 7-$CH_3$ | 225–226 |
| 32 | $CH_3$ | 7-$OCH_2CH_3$ | oil |
| 33 | $CH_2CH_3$ | 7-$OCH_2CH_3$ | oil |
| 34 | $CH_2SCH_3$ | | 88–89 |
| 35 | $CH_2SOCH_3$ | | 158–160 |
| 36 | $CH_2CH_2SCH_3$ | | 78–80 |
| 37 | $CH_2SCH_3$ | 3-Cl | 85–87 |
| 38 | $CH_2CH_2SCH_3$ | 3-Cl | 87–88 |
| 39 | $CH_2CH_2SCH_3$ | 7-$CH_3$ | 54–55 |
| 40 | $CH_2SOCH_3$ | 7-$CH_3$ | 99–103 |
| 41 | $CH_2CH_2SCH_3$ | 2-Cl | 101–102 |
| 42 | H | 7-$OCH_2CH_3$ | 180–182 |
| 43 | $CH_2CO_2CH_2CH_3$ | | 82–84 |
| 44 | H | 7-$OCH_3$ | 202–203 |
| 45 | H | 1,7-$(OCH_3)_2$ | 249–252 |
| 46 | $CH_2CH_2F$ | | 71–72.5 |
| 47 | $CF=CHI$ | | 133–136 |
| 48 | $CH_2CF_3$ | | 109–110 |
| 49 | $CH_3$ | X=S | NA |
| 50 | $CH_2CONH_2$ | X=S | NA |

*X and Z are each oxygen unless otherwise noted.

EXAMPLE A
Capsules or Tablets

| Ingredients | Quantity |
|---|---|
| A-1 | |
| Compound of Example 1 | 50 mg |
| Starch | 160 mg |
| Microcrys, Cellulose | 90 mg |
| Sodium Starch Gluctate | 10 mg |
| Magnesium Stearate | 2 mg |
| Fumed colloidal silica | 1 mg |
| A-2 | |
| Example 1 | 50 mg |
| Dicalcium Phosphate | 160 mg |
| Microcrys. Cellulose | 90 mg |
| Stearic acid | 5 mg |
| Sodium Starch Glycolate | 10 mg |
| Fumed colloidal silica | 1 mg |

The compound of Example 1 is blended into a powder mixture with the premixed exipient materials as identified above with the exception of the lubricant. The lubricant is then blended in and the resulting blend compressed into tablets or filled into hard gelatin capsules.

| EXAMPLE B Parenteral Solutions | |
|---|---|
| Ingredients | Quantity |
| Compound of Example 1 | 500 mg |
| Ethanol | 25 ml |
| Water for injection | q.s. to 100 ml |

Compound of Example 1 is added to the ethanol and mixed until the solution is clear. Water is added and the resulting solution is then filtered into the appropriate vials or ampoules and sterilized by autoclaving.

| EXAMPLE C Nasal Solutions | |
|---|---|
| Ingredients | Quantity |
| Compound of Example 1 | 500 mg |
| Propylene glycol | 30 ml |
| Benzalkonium chloride | 200 mg |
| EDTA | 200 mg |
| Water | q.s. to 100 ml |

The excipient materials are mixed and thereafter the compound of Example 1 is added and mixing is continued until the solution is clear. The water is added and the resulting solution is then filtered into the appropriate vials or ampoules.

We claim:

1. A method for treating HIV-1 infection which comprises administering, to a human infected by HIV-1, a therapeutically effective amount of a compound of the formula I wherein, X is oxygen or sulfur;

Z is oxygen or sulfur;

$R^1$ is hydrogen, alkyl of 1 to 6 carbon atoms, fluoroalkylmethyl of 1 to 3 fluorine atoms and 2 to 6 carbon atoms alkenyl or alkynyl of 2 to 6 carbon atoms, mono- or dihalovinyl, cycloalkyl of 3 to 6 carbon atoms, alkyloxyalkyl or alkylthioalkyl of 2 to 6 carbon atoms alkanoyl of 2 to 4 carbon atoms, arylmethyl or arylmethyloxy or arylcarbonyl (wherein the aryl moiety is phenyl, thienyl or furanyl, optionally substituted with methyl, methoxy or halogen), alkoxycarbonylalkyl of 3 to 6 carbon atoms aminoalkyl of 1 to 3 carbon atoms, mono- or di-alkylaminoalkyl wherein each alkyl moiety contains 1 to 2 carbon atoms, alkanoylaminoalkyl wherein the alkanoyl moiety contains 2 to 3 carbon atoms and the alkyl moiety contains 1 to 2 carbon atoms, aminocarbonylalkyl of 2 to 4 carbon atoms, mono- or dialkylaminocarbonylalkyl wherein each alkyl moiety contains 1 to 2 carbon atoms or hydroxyalkylmethyl of 2 to 6 carbon atoms;

$R^2$ is hydrogen, methyl or halogen;

$R^3$ is hydrogen, alkyl of 1 to 4 carbon atoms, halogen, hydroxyl, alkoxy of 1 to 3 carbon atoms alkylthio of 1 to 3 carbon atoms, alkanoyloxy of 2 to 3 carbon atoms, amino, alkylamino of 1 to 2 carbon atoms aminoalkyl of 1 to 2 carbon atoms, mono-or dimethylaminomethyl, hydroxyalkyl of 1 to 4 carbon atoms, alkoxyalkyl wherein each alkyl moiety contains 1 to 2 carbon atoms, alkylthioalkyl wherein each alkyl moiety contains 1 to 2 carbon atoms carboxylalkyl of 2 to 4 carbon atoms, carboxyalkoxy of 2 to 3 carbon atoms alkoxycarbonylmethyl of 3 to 4 carbon atoms or methoxycarbonylmethoxy;

$R^4$ is hydrogen, methyl or halogen; and, $R^5$ is hydrogen, alkyl of 1 to 4 carbon atoms, halogen, hydroxyl alkoxy of 1 to 3 carbon atoms alkylthio of 1 to 3 carbon atoms, alkanoyloxy of 2 to 3 carbon atoms, amino or alkylamino of 1 to 2 carbon atoms (excepting 4-amino and 4-alkylamino), aminoalkyl of 1 to 2 carbon atoms, mono-or dimethylaminomethyl, hydroxyalkyl of 1 to 4 carbon atoms, alkoxyalkyl wherein each alkyl moiety contains 1 to 2 carbon atoms carboxylalkyl of 2 to 4 carbon atoms, carboxyalkoxy of 2 to 3 carbon atoms, alkoxycarbonylmethyl of 3 to 4 carbon atoms or methoxycarbonylmethoxy;

or a pharmaceutically acceptable salt thereof.

2. The method of claim 1, wherein, in the compound of formula I

X is oxygen or sulfur;

Z is oxygen;

$R^1$ is alkyl of 1 to 5 carbon atoms, fluoroalkylmethyl of 1 to 3 fluorine atoms and 2 to 5 carbon atoms, alkenyl or alkynyl of 2 to 5 carbon atoms, mono- or dihalovinyl, cycloalkyl of 3 to 6 carbon atoms, alkyloxymethyl or alkylthiomethyl of 2 to 5 carbon atoms, alkoxyethyl or alkylthioethyl of 3 to 5 carbon atoms, alkanoyl of 2 to 3 carbon atoms, arylmethyl (wherein the aryl moiety is phenyl, thienyl or furanyl, optionally substituted with methyl, methoxy or halogen), alkoxycarbonylmethyl of 3 to 5 carbon atoms, acetylaminoalkyl wherein the alkyl moiety contains 1 to 2 carbon atoms, alkoxy of 1 to 4 carbon atom or hydroxyalkylmethyl of 2 to 5 carbon atoms;

$R^2$ is hydrogen, methyl or halogen;

$R^3$ is hydrogen, alkyl of 1 to 3 carbon atoms, halogen, hydroxyl, methoxy, ethoxy, methylthio, ethylthio, alkanoyloxy of 2 to 3 carbon atoms, amino, methylamino, aminoalkyl of 1 to 2 carbon atoms, mono- or dimethylaminomethyl, hydroxyalkyl of 1 to 3 carbon atoms, alkoxyalkyl wherein each alkyl moiety contains 1 to 2 carbon atoms, alkylthioalkyl wherein each alkyl moiety contains 1 to 2 carbon atoms, carboxylalkyl of 2 to 3 carbon atoms, carboxyalkoxy of 2 to 3 carbon atoms, alkoxycarbonylmethyl of 3 to 4 carbon atoms or methoxycarbonylmethoxy;

$R^4$ is hydrogen, methyl or halogen; and, $R^5$ is hydrogen, alkyl of 1 to 3 carbon atoms, halogen, hydroxyl, methoxy, ethoxy, methylthio, ethylthio, alkanoyloxy of 2 to 3 carbon atoms, amino or methylamino (excepting 4-amino and 4-methylamino), aminoalkyl of 1 to 2 carbon atoms, alkoxyalkyl or alkylthioalkyl wherein each alkyl moiety contains 1 to 2 carbon atoms, carboxylalkyl of 2 to 3 carbon atoms, carboxyalkoxy of 2 to 3 carbon atoms, alkoxycarbonylmethyl of 3 to 4 carbon atom or methoxycarbonylmethoxy.

3. The method of claim 1, wherein, in the compound of formula I,

X is oxygen or sulfur;

Z is oxygen;

$R^1$ is alkyl of 1 to 4 carbon atoms, fluoroalkylmethyl of 1 to 3 fluorine atoms and 2 to 4 carbon atoms, alkenylmethyl or alkynylmethyl of 2 to 4 carbon atoms, mono- or 1,2-dihalovinyl, alkoxymethyl or alkylthiomethyl of 2 to 4 carbon atoms, alkoxyethyl or alkylthioethyl of 3 to 4 carbon atoms or alkoxycarbonylmethyl of 3 to 4 carbon atoms;

$R^2$ is hydrogen, methyl or chlorine;

$R^3$ hydrogen, methyl, ethyl, chlorine, bromine, hydroxyl, methoxy, methylthio, acetyloxy, amino, methylamino, aminomethyl, hydroxymethyl, hydroxyethyl, methoxymethyl or methylthiomethyl;

$R^4$ is hydrogen, methyl or chlorine; and, $R^5$ is hydrogen, methyl, ethyl, chlorine, bromine, hydroxyl, methoxy, methylthio, acetyloxy, amino or methylamino (excepting 4-amino and 4-methylamino), aminomethyl, hydroxymethyl, hydroxyethyl, methoxymethyl or methylthiomethyl.

4. The method of claim 1, wherein, in the compound of formula I,

X is oxygen or sulfur;

Z is oxygen;

$R^1$ is alkyl of 1 to 4 carbon atoms, fluoroalkylmethyl of 1 to 3 fluorine atoms and 2 to 4 carbon atoms, alkenylmethyl or alkynylmethyl of 2 to 4 carbon atoms, mono- or 1,2-dihalovinyl, alkoxymethyl or alkylthiomethyl of 2 to 4 carbon atoms, alkoxyethyl or alkylthioethyl of 3 to 4 carbon atoms or alkoxycarbonylmethyl of 3 to 4 carbon atoms;

$R^2$ and $R^4$ are each hydrogen;

$R^3$ is hydrogen or 7-methyl; and, $R^5$ is hydrogen or 2-amino.

5. The method of claim 4, further characterized in that $R^1$ is hydrogen, methyl, ethyl, propyl, isopropyl or allyl.

* * * * *